(12) United States Patent
Mahoney et al.

(10) Patent No.: US 7,992,803 B2
(45) Date of Patent: Aug. 9, 2011

(54) NEBULIZER HAVING A HIGH EFFICIENCY IMPACTOR

(75) Inventors: Derek D. Mahoney, Manalapan, NJ (US); George V. Muttathil, Cherry Hill, NJ (US); Kerry D. O'Mara, Hopewell Township, NJ (US); Albert F. Stevens, Moorestown, NJ (US)

(73) Assignee: Stevens Medical, LLC, Moorestown, NJ (US)

( * ) Notice: Subject to any disclaimer, the term of this patent is extended or adjusted under 35 U.S.C. 154(b) by 140 days.

(21) Appl. No.: 12/259,820

(22) Filed: Oct. 28, 2008

(65) Prior Publication Data

US 2009/0272376 A1 Nov. 5, 2009

Related U.S. Application Data

(60) Provisional application No. 60/984,146, filed on Oct. 31, 2007.

(51) Int. Cl.
*B05B 7/30* (2006.01)
(52) U.S. Cl. .......................... 239/318; 239/338; 239/344
(58) Field of Classification Search .................. 239/302, 239/303, 307, 308, 318, 344, 368, 370, 398, 239/417.5, 425.5, 432, 338
See application file for complete search history.

(56) References Cited

U.S. PATENT DOCUMENTS

| | | | |
|---|---|---|---|
| 2,726,896 A * | 12/1955 | McKinnon | ................... 239/335 |
| 4,228,795 A | 10/1980 | Babington | |
| 4,509,688 A | 4/1985 | Gagne et al. | |
| 4,809,706 A | 3/1989 | Watson et al. | |
| 5,660,167 A | 8/1997 | Ryder | |
| 5,678,563 A | 10/1997 | Addington et al. | |
| 5,904,656 A | 5/1999 | Addington et al. | |
| 6,004,268 A | 12/1999 | Addington et al. | |
| 6,267,729 B1 | 7/2001 | Addington et al. | |
| 6,405,944 B1 | 6/2002 | Benalikhoudja | |
| 6,561,195 B2 | 5/2003 | Addington et al. | |
| 6,568,397 B1 | 5/2003 | Addington et al. | |
| 6,581,605 B2 | 6/2003 | Addington et al. | |
| 6,655,376 B2 | 12/2003 | Addington et al. | |
| 6,679,249 B2 | 1/2004 | Addington et al. | |
| 6,859,272 B2 | 2/2005 | Rutzke et al. | |
| 6,883,517 B2 | 4/2005 | Halamish | |
| 6,994,083 B2 | 2/2006 | Foley et al. | |
| 7,013,894 B2 | 3/2006 | McFarland, Jr. | |
| 7,029,656 B2 | 4/2006 | Coifman | |

(Continued)

FOREIGN PATENT DOCUMENTS

WO 9953837 10/1999
(Continued)

OTHER PUBLICATIONS

International Search Report dated Dec. 29, 2008 relating to corresponding PCT/US2008/081451.

(Continued)

*Primary Examiner* — Davis Hwu
(74) *Attorney, Agent, or Firm* — Niels Haun; Dann Dorfman Herrell & Skillman, PC

(57) ABSTRACT

The present invention relates generally to a nebulizer, and more particularly but not exclusively to a compact nebulizer that may include an angled impactor and/or siphon tube integrated into the impactor to increase the nebulizer efficiency.

2 Claims, 15 Drawing Sheets

U.S. PATENT DOCUMENTS

| | | |
|---|---|---|
| 7,036,500 B2 | 5/2006 | Niles et al. |
| 7,073,731 B2 | 7/2006 | Hess et al. |
| 7,080,643 B2 | 7/2006 | Grychowski et al. |
| 7,129,619 B2 | 10/2006 | Yang et al. |
| 7,131,439 B2 | 11/2006 | Blacker et al. |
| 7,229,028 B2 | 6/2007 | Chen et al. |
| 7,267,120 B2 | 9/2007 | Rustad et al. |
| 7,559,322 B2 | 7/2009 | Foley et al. |
| 2001/0003143 A1 | 6/2001 | Addington et al. |
| 2001/0050086 A1 | 12/2001 | Addington et al. |
| 2002/0100476 A1 | 8/2002 | Addington et al. |
| 2002/0104529 A1 | 8/2002 | Addington et al. |
| 2003/0089366 A1 | 5/2003 | Sommer |
| 2004/0050952 A1 | 3/2004 | Chen et al. |
| 2004/0060556 A1 | 4/2004 | Halamish |
| 2004/0181161 A1 | 9/2004 | Addington et al. |
| 2006/0213507 A1 | 9/2006 | Foley et al. |
| 2007/0107725 A1 | 5/2007 | Addington et al. |
| 2007/0123793 A1 | 5/2007 | Addington et al. |
| 2007/0137648 A1 | 6/2007 | Addington et al. |
| 2007/0163572 A1 | 7/2007 | Addington et al. |
| 2008/0283049 A1 | 11/2008 | Mahoney et al. |

FOREIGN PATENT DOCUMENTS

| | | |
|---|---|---|
| WO | 0218001 | 3/2002 |

OTHER PUBLICATIONS

Written Opinion dated Dec. 29, 2008 relating to corresponding PCT/US2008/081451.
Newman, S.P., et al., "Deposition of pressurized aerosols in the human respiratory tract," Thorax, 1981, 36:52-55.
William Hinds, Aerosol Technology p. 241 (1999).
International Preliminary Report on Patentability in International Application No. PCT/US2008/081451 dated May 14, 2010.
International Search Report and Written Opinion dated Aug. 19, 2008 in Application No. PCT/US08/55117.
International Preliminary Report on Patentability in International Application No. PCT/US2008/055117 dated Sep. 11, 2009.
International Search Report from corresponding application PCT/US08/73721 dated Nov. 6, 2008.
Written Opinion from corresponding application PCT/US08\73721 dated Nov. 6, 2008.
International Preliminary Report on Patentability in International Application No. PCT/US2008/073721 dated May 20, 2010.
Official Action from U.S. Appl. No. 12/038,505 dated Oct. 1, 2010.

\* cited by examiner

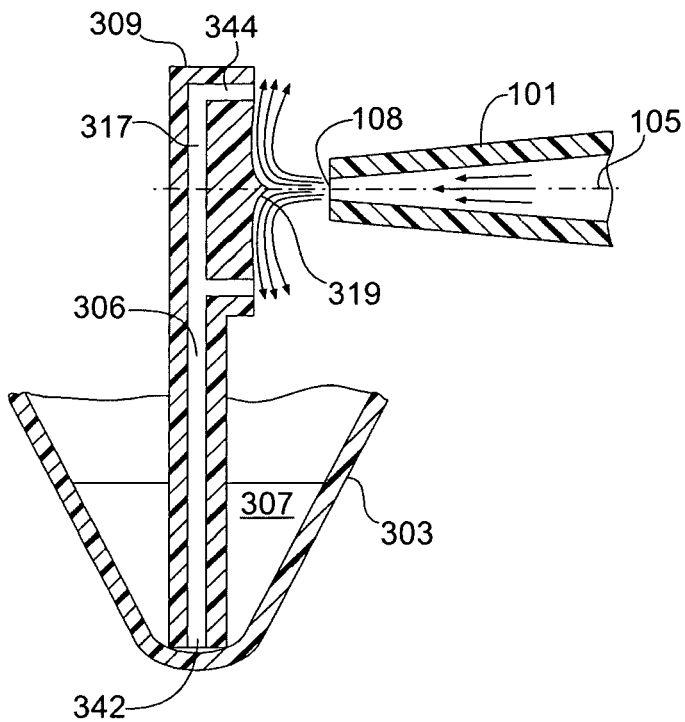
Fig. 16
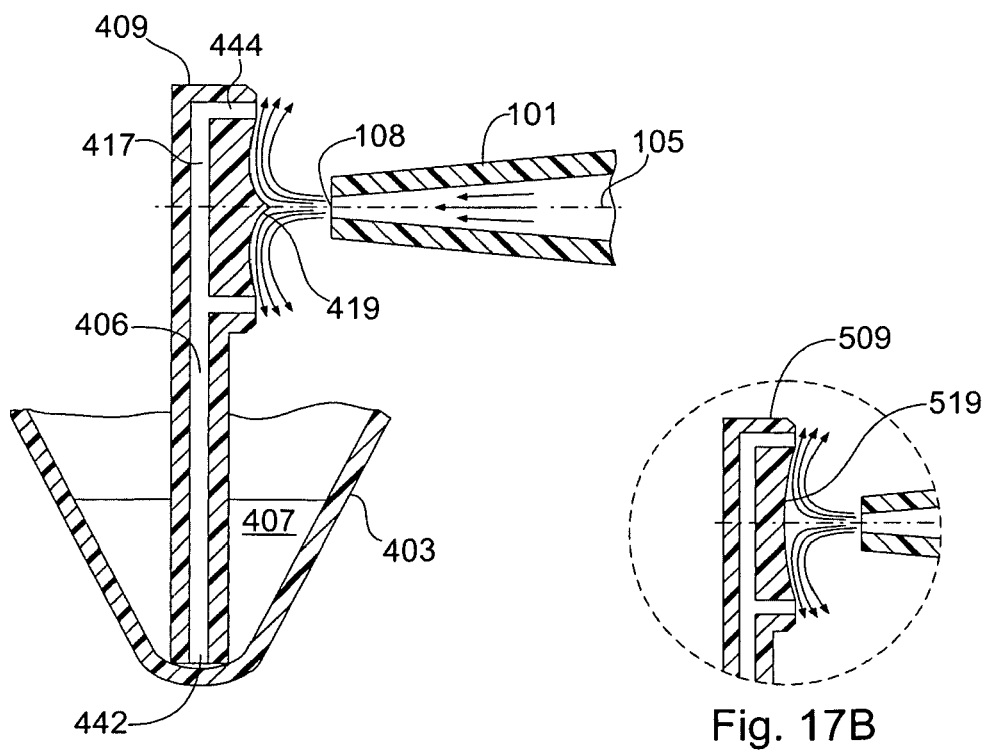
Fig. 17A
Fig. 17B

NEBULIZER HAVING A HIGH EFFICIENCY IMPACTOR

RELATED APPLICATIONS

This application claims benefit of U.S. Provisional Application Ser. No. 60/984,146, filed Oct. 31, 2007, entitled "Nebulizer Having A High Efficiency Impactor," the entire contents of which are incorporated herein by reference.

FIELD OF THE INVENTION

The present invention relates generally to a nebulizer, and more particularly but not exclusively to a compact nebulizer that may include an angled impactor and/or siphon tube integrated into the impactor.

BACKGROUND OF THE INVENTION

The deposition efficiency in the tracheobronchial (TB) and pulmonary regions is highly dependent on particle size. Particle sizes in the range of about 1 to 5 μm, as well as the size range extending from approximately 0.005 to 0.5 μm, have a relatively high rate of deposition within the aforementioned regions. (See William Hinds, Aerosol Technology, p 241 (1999).) Various methods have typically been used to generate these therapeutic fine particles, such as air-blast nebulizers (i.e., compressed air, jet, or venturi nebulizer), pressure nebulizers, ultrasonic nebulizers, a vibrating orifice, a spinning disk, condensation devices, and inkjet technology-based nebulizers. However, despite the variety of methods used to generate therapeutic fine particles, problems remain such as wasted medication that is not dispensed and the swallowing of liquid medication by the user. Currently available nebulizers typically have residual (i.e., waste) medication of 50% or more. This waste is largely due to the fact that existing nebulizers will generate and disperse large and small particles. The large particle dispersion is not well controlled and leads to residual medication in the nebulizer and associated apparatus. Additionally, some nebulizers are relatively bulky, which unfortunately provides considerable surface area for medication deposition within the device which in turn leads to wasted unused medication. Thus, it would be an advance in the state of nebulizer art to more efficiently dispense and utilize liquid medication to reduce waste and increase patient compliance, and to protect the user of the nebulizer from swallowing liquid medication.

SUMMARY OF THE INVENTION

The present invention provides in one of its aspects a reduction in the necessary treatment time through the generation of a dense mist of particles, in part because the particles are in the correct size range for effective deposition in the desired TB or pulmonary regions. The relatively higher density of nebulized particles may be created with the use of multiple jet impactors. Within a single nebulizer assembly high velocity jets of liquid-carrying gas may be directed at an impactor surface, creating a relatively higher density of fine droplets. Thus, the patient can inhale the full dose of medicine in a shorter time from which three benefits follow: more rapid treatment in critical situations, a financial benefit for the clinical setting (i.e., less time required from medical staff), and higher patient compliance in the home setting.

In one of its aspects, the present invention provides a nebulizer for delivering a mist of liquid, comprising a housing and a reservoir disposed internally to the housing for containing a liquid to be nebulized by the nebulizer. Depending on the application the liquid may desirably be a liquid medication. The nebulizer may include a nebulizer tube having a gas channel. The gas channel may include a first end for receiving gas, such as a compressed gas, and a second end for expelling compressed gas. The gas channel may extend along a longitudinal axis from a first end to a second end of the nebulizer tube. The nebulizer tube may also include a liquid feed channel having a first end in fluid communication with the reservoir for receiving the liquid from the reservoir and having a second end disposed proximate the second gas channel end. An impactor may be disposed proximate the second end of the nebulizer tube, with the impactor having an impaction surface disposed at an inclined, non-orthogonal angle relative to the longitudinal axis of the nebulizer tube. Expulsion of compressed gas from the second end of the gas channel onto the impactor can create a siphon in the liquid feed channel to draw liquid into the feed channel and to expel the liquid and compressed gas from the second end of the nebulizer tube to nebulize the expelled liquid when the expelled liquid strikes the impactor.

In another of its aspects, the present invention provides a nebulizer for delivering a mist of liquid, comprising a housing and a reservoir disposed internally to the housing for containing a liquid to be nebulized by the nebulizer. The nebulizer may include a gas channel disposed within the housing, the channel including a first end for receiving gas, such as a compressed gas, and a second end for expelling compressed gas. An impactor may be disposed proximate the second end of the gas channel. The impactor may include a liquid feed channel having a first end in fluid communication with the reservoir for receiving liquid from the reservoir and may have a second end disposed proximate the second gas channel end. Expulsion of compressed gas from the second end of the gas channel onto the impactor can create a siphon in the liquid feed channel to draw liquid into the feed channel and to expel the liquid from the second end of the liquid feed channel to nebulize the expelled liquid.

BRIEF DESCRIPTION OF THE DRAWINGS

The foregoing summary and the following detailed description of the preferred embodiments of the present invention will be best understood when read in conjunction with the appended drawings, in which:

FIG. 16 schematically illustrates a fragmentary side cross-sectional view of yet another exemplary impactor in accordance with the present invention having in integrated siphon tube and a cusp-shaped impactor surface disposed proximate an exit nozzle;

FIGS. 17A and 17B schematically illustrate fragmentary side cross-sectional views of a further exemplary impactor in accordance with the present invention having in integrated siphon tube and a concave impactor surface disposed proximate an exit nozzle;

DETAILED DESCRIPTION OF THE INVENTION

Figure 1:
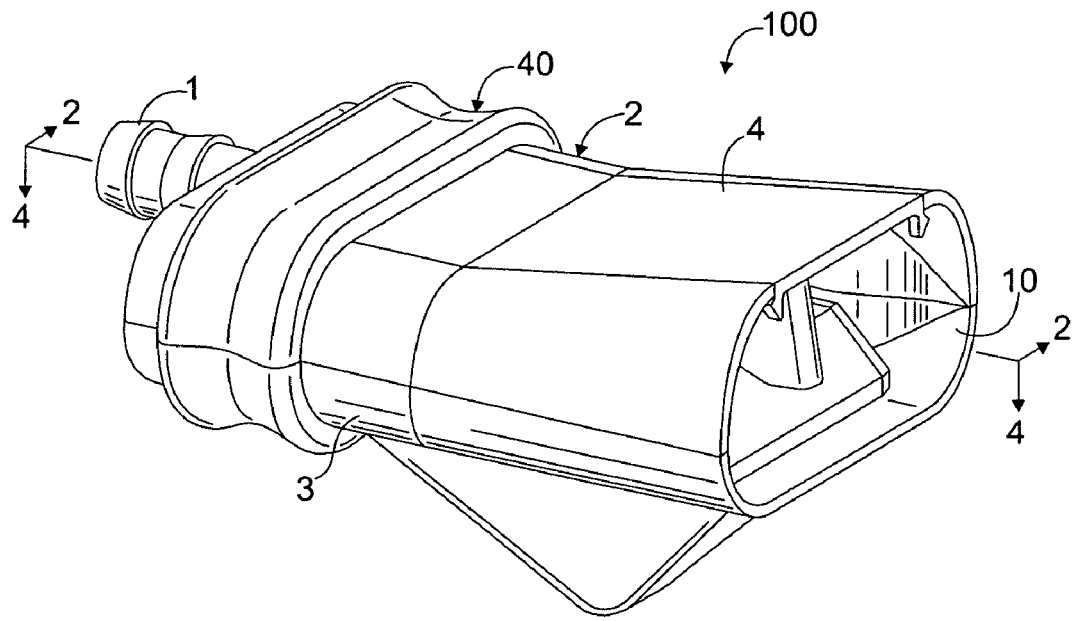
FIG. 1 schematically illustrates a perspective view of a first exemplary nebulizer of the present invention.
Figure 2:
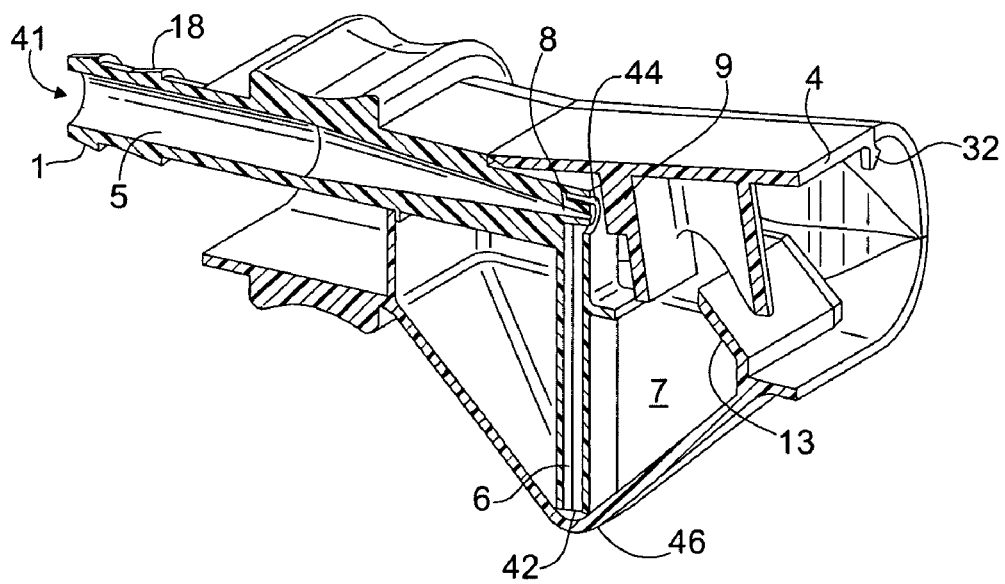
FIG. 2 schematically illustrates a cross-sectional view of the nebulizer of FIG. 1 taken along the sectioning line 2-2.

Referring now to the figures, wherein like elements are numbered alike throughout, FIGS. 1 and 2 illustrate an external view of a first configuration of a nebulizer 100 of the present invention. The nebulizer 100 comprises a nebulizer tube 1 disposed within a housing 40 for receiving compressed gas, such as compressed air or nitrogen, for example, and an exit port 10 for delivering a nebulized mist to a user. The housing 40 may comprise an upper housing 2 and a lower housing 3, which may be registered to one another by cooperation between holes 21 of the lower housing 3 and press-fit pins 20 of the upper housing 2 to permit attachment of the upper housing 2 to the lower housing 3 without the use of adhesives or separate fasteners, FIGS. 10, 11. The nebulizer tube 1 may be monolithically formed as a part of either the upper or the lower housing 2, 3, FIG. 2. As such, the nebulizer 1 may desirably include only two pieces, the upper housing 2 and lower housing 3.

Figure 8:
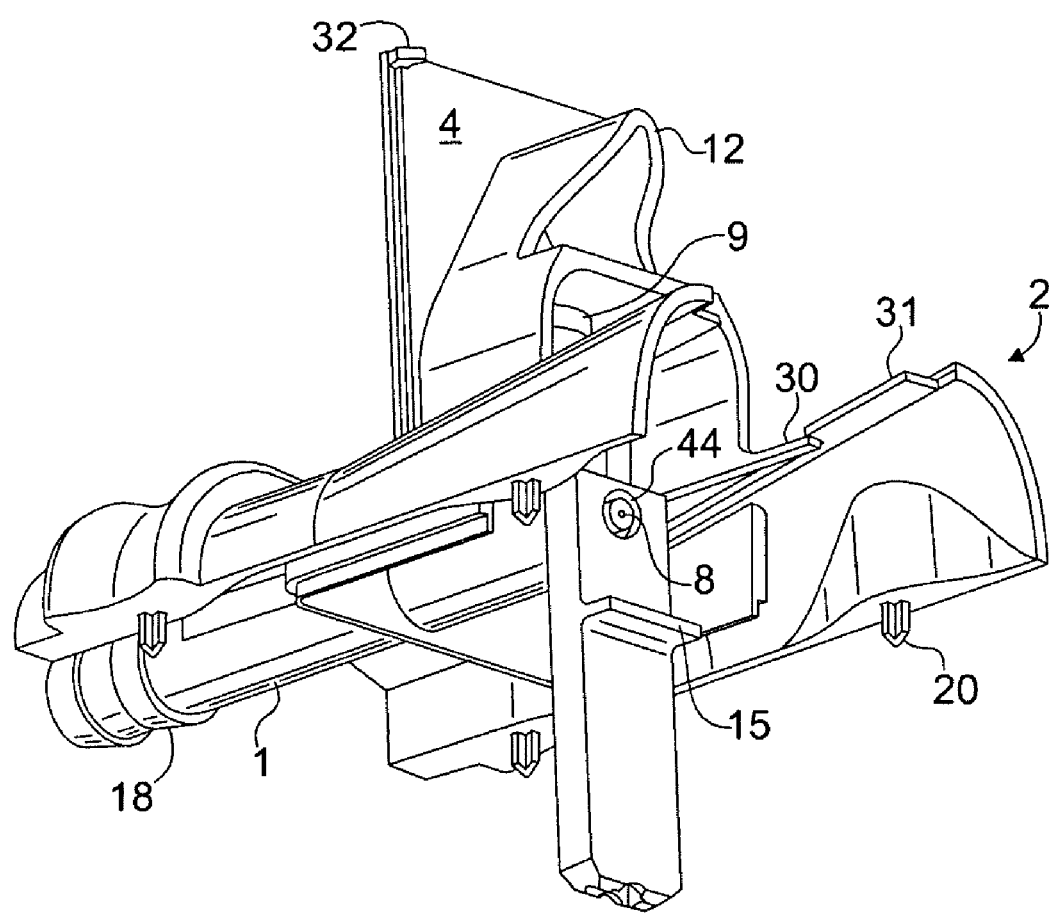
FIG. 8 schematically illustrates a perspective view of the upper housing of the nebulizer of FIG. 1 with the lid shown in a partially opened position.
Figure 9:
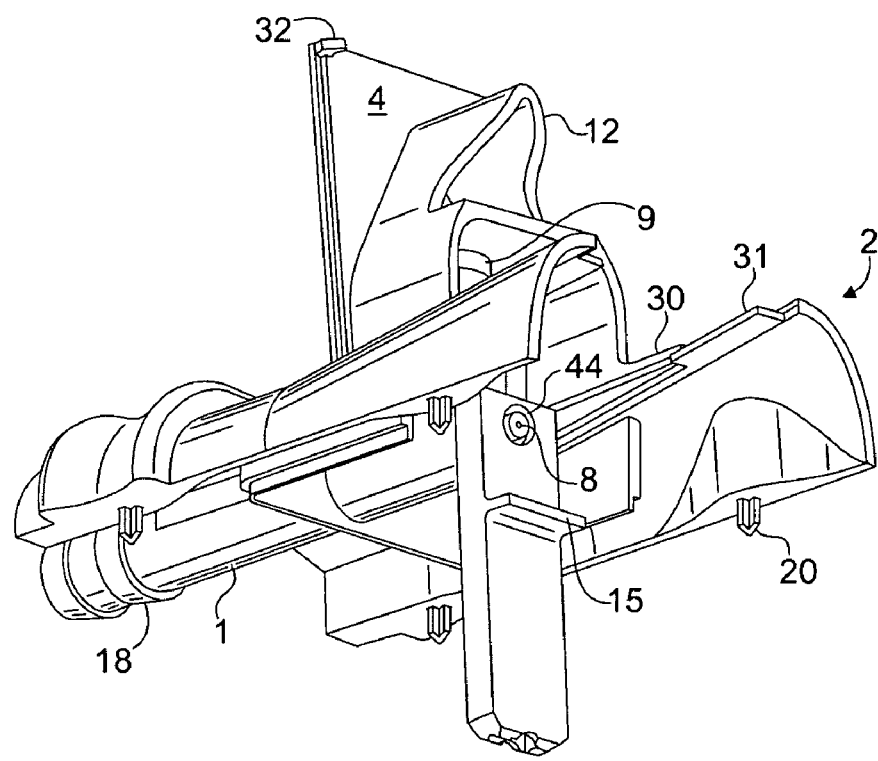
FIG. 9 schematically illustrates a perspective view of the upper housing of the nebulizer of FIG. 8 but with the lid shown in a more fully opened position.
Figure 10:
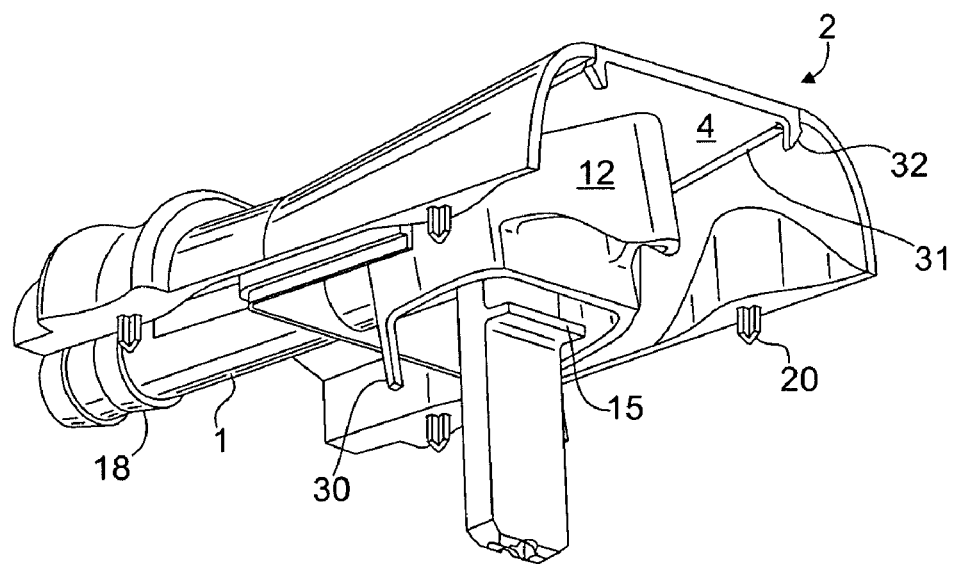
FIG. 10 schematically illustrates a perspective view of the upper housing of the nebulizer of FIGS. 8 and 9 but with the lid shown in the closed position.
Figure 11:
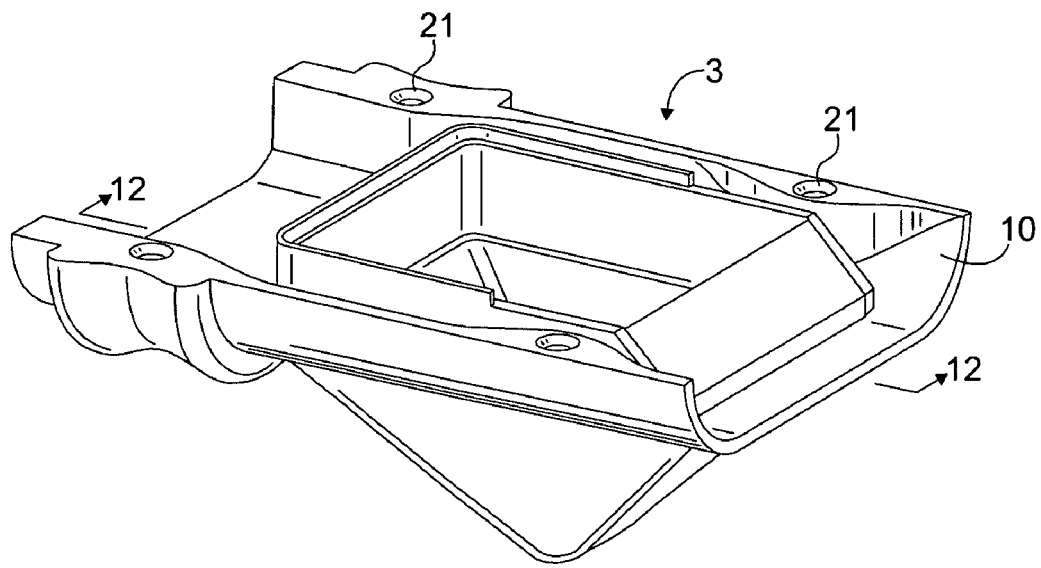
FIG. 11 schematically illustrates a perspective view of the lower housing of the nebulizer of FIG. 1.
Figure 12:
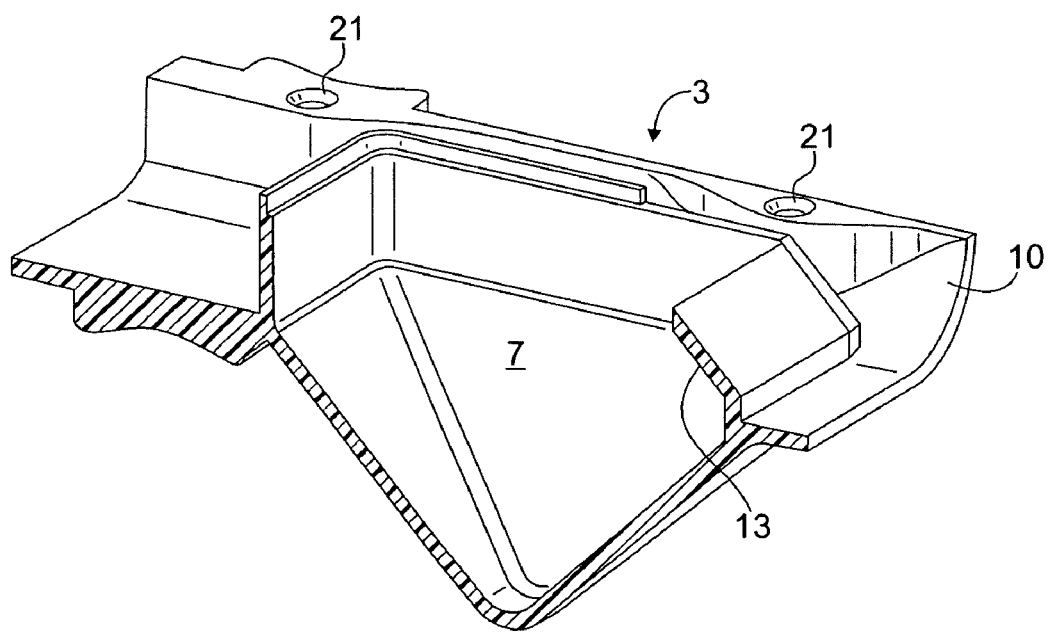
FIG. 12 schematically illustrates a cross-sectional view of the lower housing of FIG. 11 taken along the sectioning line 12-12.

The upper housing 2 may include a lid 4 for introducing a liquid medication into the housing 40. The lid 4 may be provided as a monolithic part of the upper housing 2 and may be movable by attachment via a living hinge 45. To assist in maintaining the lid 4 in an opened position to facilitate filling of the nebulizer 100, the lid 4 may include a protruding beam 30 that interacts with shelf 31 of the upper housing 2, FIGS. 5-9. Referring specifically to FIGS. 8 and 9, the interaction of the beam 30 and the shelf 31 may be understood. For example, FIG. 8 shows the lid 4 of the nebulizer 100 in a partially opened position such that the beam 30 is in contact with the underside of the shelf 31. In this respect, the beam 30 has a length sufficiently long to permit the tip of the beam 30 to catch underneath the shelf 31 while still permitting the beam 30 to snap past the shelf 31 to rest on the upper surface of the shelf 31. That is, by continuing to open the lid 4 the beam 30 can snap through and rest on the upper surface of the shelf 31 as shown in FIG. 9, thus preventing the lid 4 from closing accidentally. After filling the nebulizer 100, the lid 4 may closed as shown in FIG. 10. The lid latch 32 assists in preventing the lid 4 from inadvertently opening during use. In addition, an optional key 138 and slot 139 may be provided in an optional configuration of the upper housing 102, FIG. 13.

To receive a liquid, such as medication, introduced through the lid 4, the lower housing 3 includes a reservoir 7 for containing the liquid medication within a localized region within the lower housing 3. (While any suitable liquid may be provided in the reservoir, for illustration purposes the devices of the present application are described herein as containing a medication.) The reservoir 7 may be dimensioned to hold at least 3 ml of liquid medication, for example. The reservoir 7 may be generally V-shaped and may include a trough 46 into which the liquid medication can pool and over which the inlet end 42 of the feed tube 6 may be positioned to receive the pooled medication, FIG. 2. Alternatively, the reservoir 7 may include shapes such as cylindrical, spherical, a rectangular, for example. Maintaining the liquid medication in a specified location assists in making the medication available to the nebulizer tube 1, and thus aids in efficient use of the medication. The inlet end 42 of the feed tube 6 may meet with the geometry of the reservoir 7 in the lower housing 3 such that medication in the reservoir 7 is wicked to the bottom of the feed tube 6 so that nearly all the medication can be siphoned into the air stream. The flat sloping walls that form the reservoir 7 allow the medication to be fully consumed even when the user is reclined at a significant angle.

The geometry of the reservoir walls, together with the wetting characteristics of the reservoir can also help to reduce the amount of residual unused medication. Internal angles or grooves that run in a direction down the side walls of the reservoir 7 can also be included. The dimensions of the angles or grooves can be relatively small as compared with the dimensions of the reservoir 7, in which case the liquid will "wick" along the angles or grooves. Further, the design can be made to cause the liquid to preferentially move in one direction along the length of these features by gradually changing the size or shape of the groove along its length. For example, if the internal angle of the groove becomes more acute, the liquid will be preferentially pulled in that direction. Another technique for pulling the liquid toward the feed channel inlet 42 of the feed channel 6 is by make the gap between the bottom surface of the reservoir 7 and the feed channel inlet 42 sufficiently small to wick into this gap (if the surfaces are wetting materials). A further aid is to have the gap reduce in size (taper, or converge) as the liquid moves in the flow-wise direction, towards the feed channel inlet 42. A gap that becomes smaller as it approaches the inlet to the feed channel 42 can encourage the liquid to flow in that direction.

Figure 13:
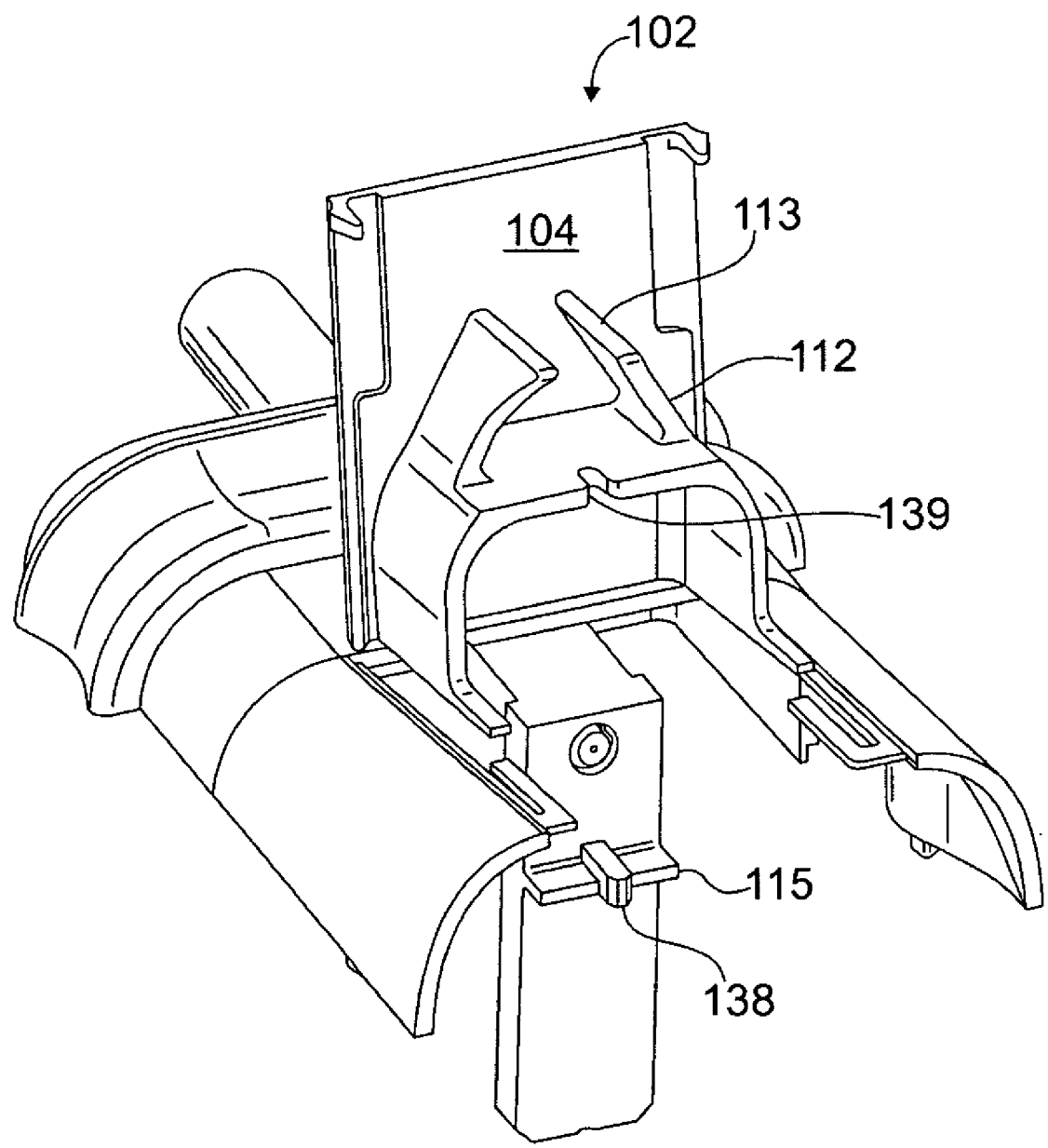
FIG. 13 schematically illustrates a perspective view of an additional configuration of the upper housing of the present invention with the lid shown in an opened position.

To assist in preventing the liquid medication from spilling out of the reservoir 7 through the exit port 10, an overflow wall 13 may be provided proximate the exit port 10 to help deter introduction of liquid medication into the user's mouth, FIGS. 2, 13. The medication overflow wall 13 may allow the user to be inclined in bed or reclining while using this device. Furthermore, one or more semi-permeable membranes may be provided at the exit port 10 of the nebulizer 100 to permit mist flow while acting as an effective liquid barrier, thus creating a safety feature that prevents a user from swallowing liquid medication contained in the nebulizer 100. For instance, in the event that the nebulizer is tilted beyond some critical angle during use, the membrane will block the flow of medication into the user's mouth while permitting the nebulized mist to flow through the membrane. For example, a foam sponge material may be used as the membrane to permit mist flow while deterring liquid medication flow therethrough.

The nebulizer tube 1 includes a gas channel 5 that includes an inlet end 41 for connection to a source of compressed air, and may be provided in the form of a convergent channel 5 that has a cross-sectional dimension that decreases from the inlet end 41 to the outlet end, or throat 8, where the cross-sectional dimension may be a minimum, e.g., 15 to 20 mils (thousandths of an inch). The inlet end 41 of the nebulizer tube 1 may include a barb 18 to assist in securing attachment of a compressed air hose to the inlet end 41 of the nebulizer tube 1, FIGS. 1, 2. The nebulizer tube 1 also includes a liquid feed channel 6 having an inlet end 42 disposed in fluid communication with the reservoir 7 to receive liquid medication disposed within the lower housing 3, FIGS. 2, 3. The liquid feed channel 6 has an annular medication exit port 44, or outlet end, of the liquid feed channel 6 disposed proximate the throat 8 of the gas channel 5. The liquid feed channel 6 may have a generally rectangular or circular cross-sectional shape and have a cross-sectional dimension of 30-90 mils. An air baffle 15 may be provided on the nebulizer tube 1 intermediate the feed channel inlet end 42 and the throat 8, so that the high-velocity mixture striking the impactor 9 does not blow liquid away from the feed channel inlet 42 which could lead to a feed channel starvation condition. (The optional key 138 on the baffle 115 may prevent excessive disturbance of fluid in the reservoir 7 due to the impinging of high-velocity air onto the liquid surface, FIG. 13.) In addition, inclusion of the air baffle 15 can deter unwanted formation of large airborne droplets that might result from the surface of the liquid being agitated.

The throat 8 is oriented so that the output flow from the throat 8 strikes an impactor 9, which may be provided as a monolithic part of the upper housing 2. This energetic collision generates the very fine, therapeutic particles required of nebulizers. It has been determined that a sufficiently small spacing is required between the throat 8 and impactor 9 to generate a fine mist. A suitable spacing from the outlet end of the nebulizer tube 1 to the impactor 9 is 10 to 30 mils, though larger distances may be used, e.g., 80 mils. The impactor 9 may be disposed at a non-orthogonal angle relative to the longitudinal axis of the gas channel 5 to direct the air flow exiting the throat 8 downward towards the reservoir 7, although a portion of the flow may also be directed upwards and laterally. For example, the impactor 9 may be disposed at an angle of approximately 81° relative to the longitudinal axis of the gas channel 5.

Figure 23:
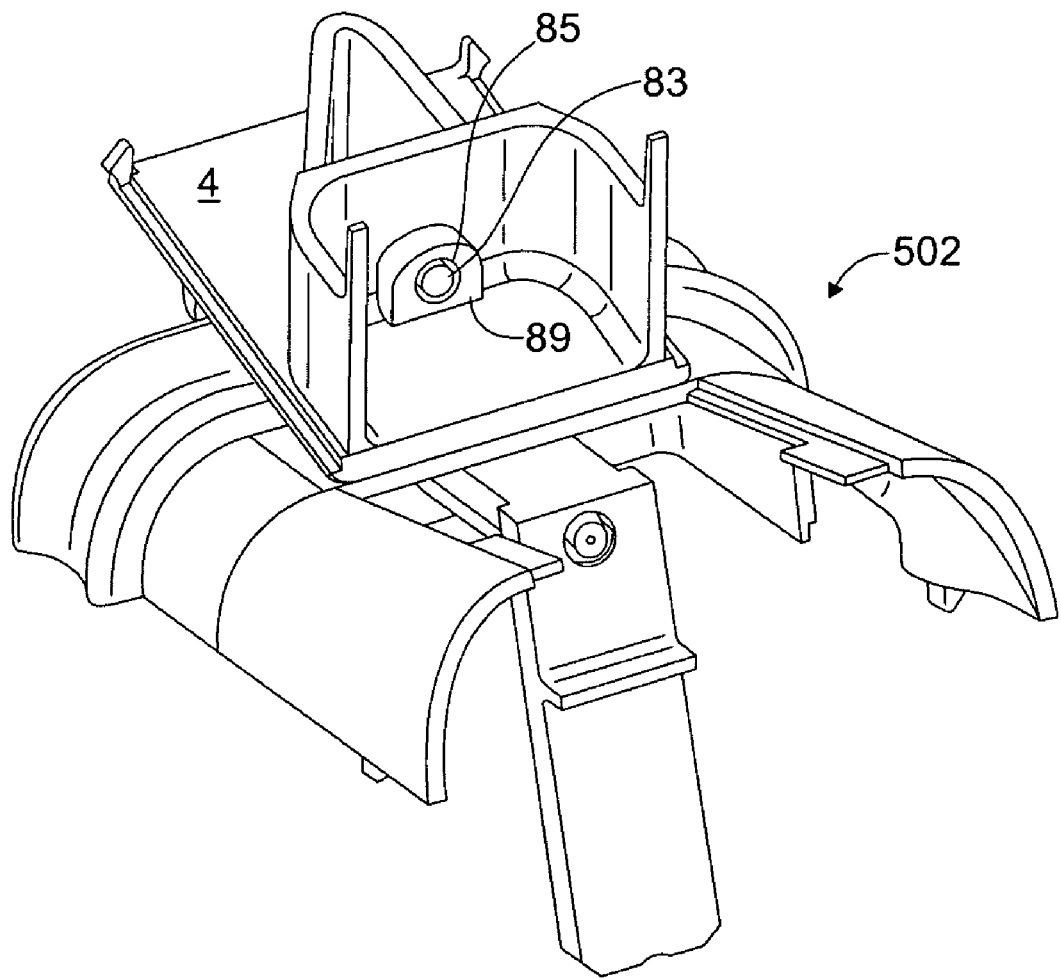
FIG. 23 schematically illustrates a perspective view of an upper housing with the lid shown in an opened position in which the impactor includes an annular trough.

The impactor 9 may have a height that changes abruptly to provide a mesa-type shape, which has been demonstrated to yield a relatively-high nebulization efficiency, especially in combination with the angled impactor orientation. It is believed that the turbulence that is generated as the air flow detaches from the edge of the mesa enhances efficiency. The impaction surface of the mesa may be flat, convex, concave, or some other non-planar structure. The edges of the mesa may incorporate jagged features to further enhance efficiency. In addition, the impactor 9 may have the shape other than a mesa, such as a spherical or cylindrical shape. For example, a ring feature may be added about a mesa 83 to facilitate the creation of a resonant annular channel 85 in the impactor 89 of an upper housing 502, FIG. 23. The fundamental resonant frequency of the annular channel 841 may be tuned to help generate particles of a preferred size. Also, the annular channel 85 can create more turbulence to increase efficiencies.

The surface of the impactor 9 may be roughened to further enhance nebulization. The roughness may be provided in the form of small-scale concentric ridges disposed on the impaction surface of the impactor 9. Alternatively, the impaction surface of the impactor 9 may have a sandpaper-like roughness on the order of 150 to 220 grit sandpaper, which appears to improve the size and throughput of the generated mist. Several mechanisms of fluid dynamics can be cited as possible reasons for the roughness effect. First, the roughness may help to provide momentum mixing between the higher speed air flow near the impactor surface and the laminar sub layer that is even closer to the surface. Mixing of these layers affords boundary layer and flow control, which is used extensively in aerodynamic designs. In the present case, the boundary layer mixing will create higher shear stress. Higher shear stress can be more capable of dislodging small quantities of liquid from the rough surface. In addition, once particles are airborne, a higher shear stress might also provide a lift force through the Safferman effect. This would tend to keep particles away from the impactor surface and help reduce settling. This explanation is looking at the flow situation from a generally steady-state perspective. Second, if the rough surface is a "wetting" material, then a layer of liquid will constantly be drawn to cover it. Thus, a thin layer of liquid will also be drawn to cover the small-scale protrusions or "peaks." At the same time, these peaks protrude into an airflow that is generally moving parallel to the impactor surface. This can cause localized vortex-shedding and non-steady pressures.

In operation, a high pressure gas (typically air) of 25 to 45 psi, for example, enters the nebulizer tube 1 through the inlet end 41 and is accelerated to sonic velocity and expands as it leaves the throat 8. Since the feed channel 6 is in communication with a reservoir 7 of liquid (typically medication), under the proper conditions, liquid medication is siphoned through the feed channel 6 and exits the nebulizer tube 1 via annular medication exit port 44. Whether siphoning occurs depends on the spacing between the exit port 44 and the impactor 9. Provided that the spacing between the exterior face of the nozzle 8 and the impactor 9 is sufficiently small (for example, 30 mils), a low-pressure air zone will be formed proximal to the annular medication exit port 44. This creates a pressure differential that will siphon fluid from the reservoir 7 and direct it towards the impactor 9. The energy imparted to the liquid from the gas, as well as the energetic collision on the impactor 9, generates fine particles from the liquid. Because the throat 8 and impactor 9 are both monolithic to the upper housing 2, the spacing between the throat 8 and the impactor 9 is very repeatable.

Figure 3:
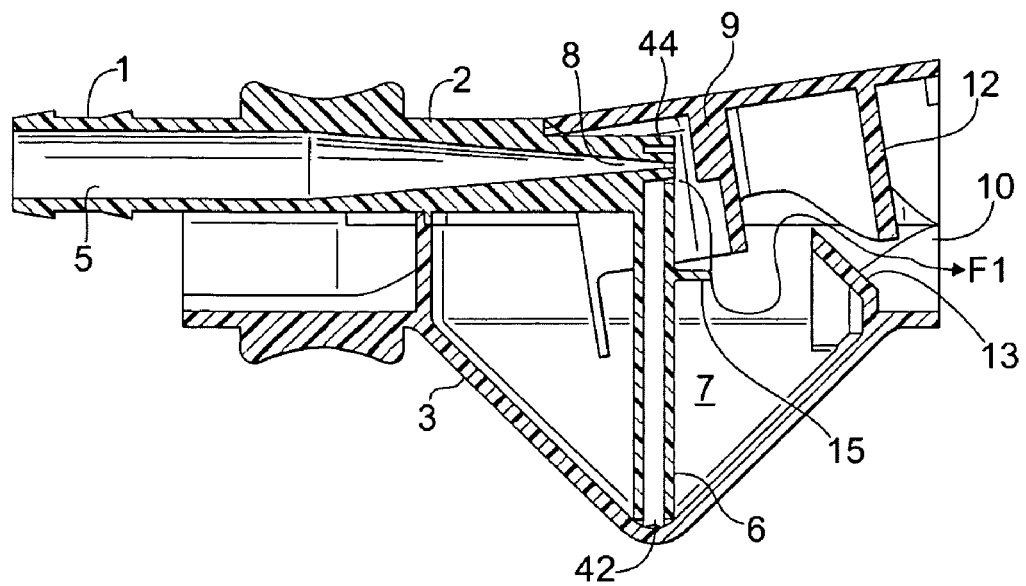
FIG. 3 schematically illustrates a side view of the cross-sectional view of the nebulizer of FIG. 2 showing a flow path for the nebulized particles.
Figure 4:
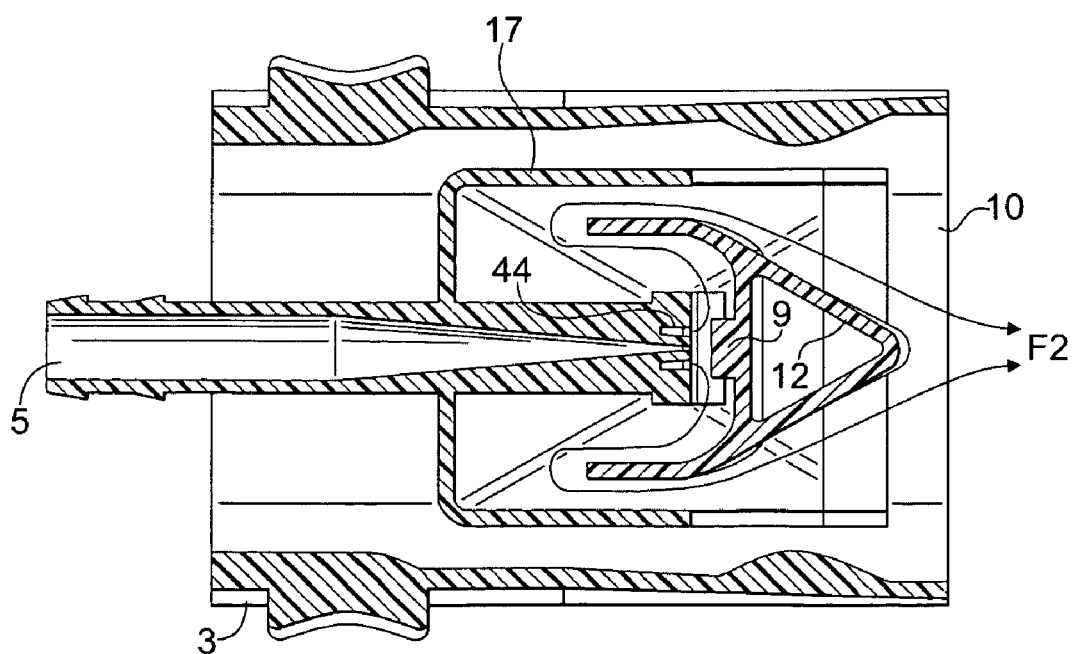
FIG. 4 schematically illustrates a cross-sectional view of the nebulizer of FIG. 1 taken along the sectioning line 4-4 showing a flow path for the nebulized particles.
Figure 5:
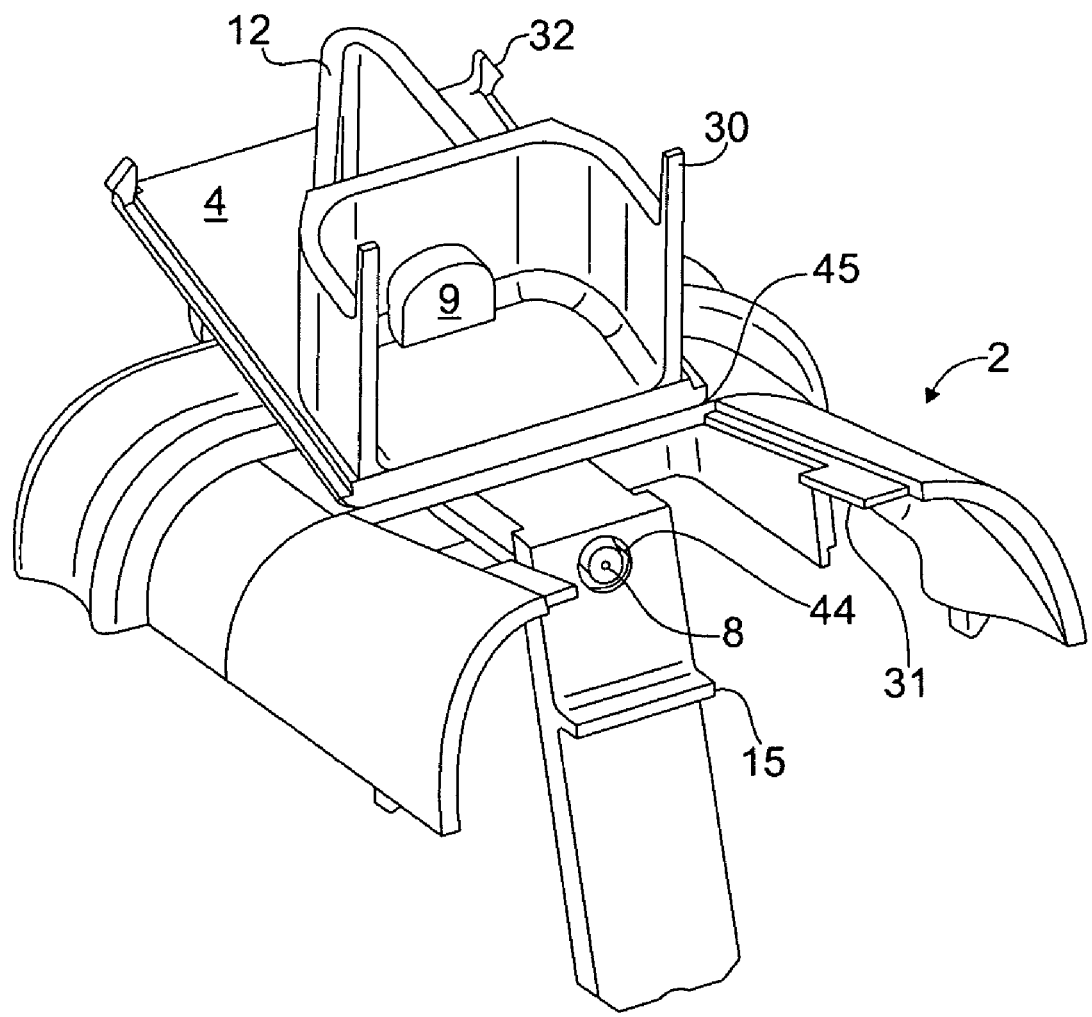
FIG. 5 schematically illustrates a perspective view of the upper housing of the nebulizer of FIG. 1 with the lid shown in an opened position.
Figure 6:
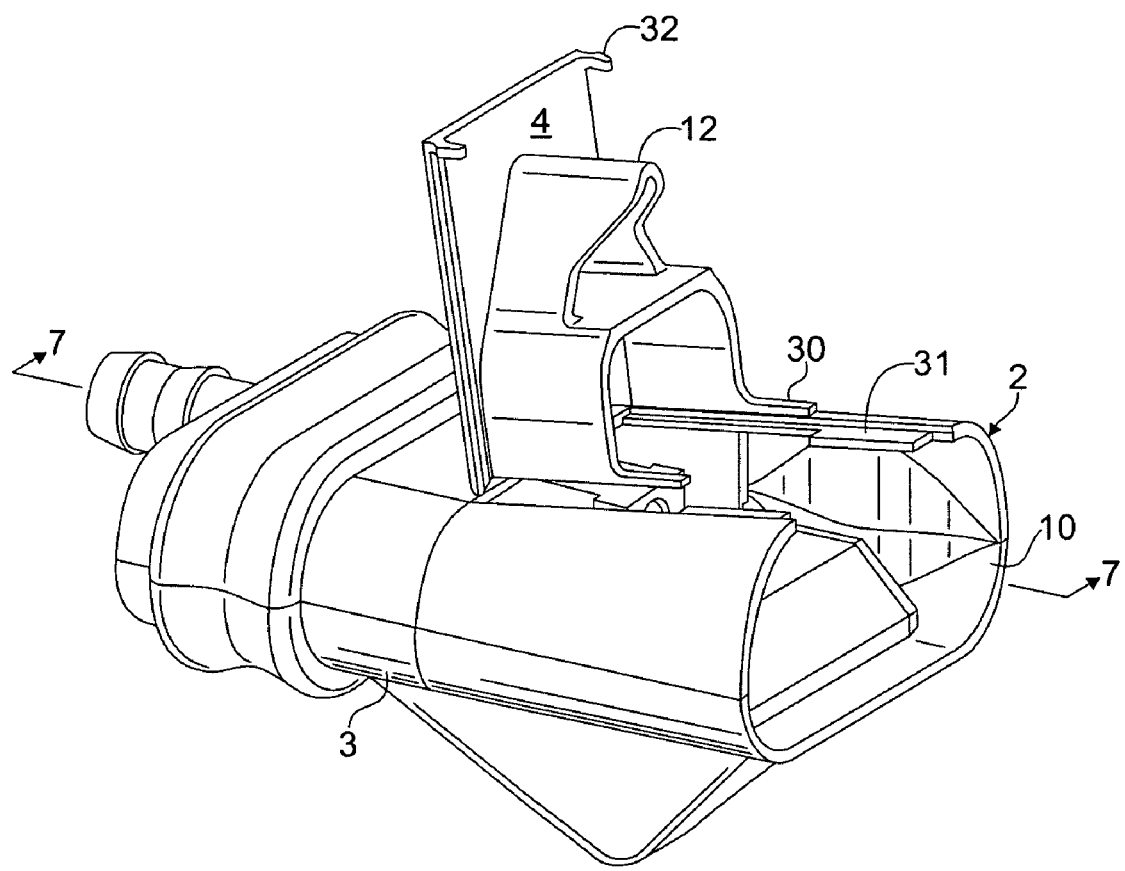
FIG. 6 schematically illustrates a perspective view of the nebulizer of FIG. 1 with the lid shown in an opened position.
Figure 7:
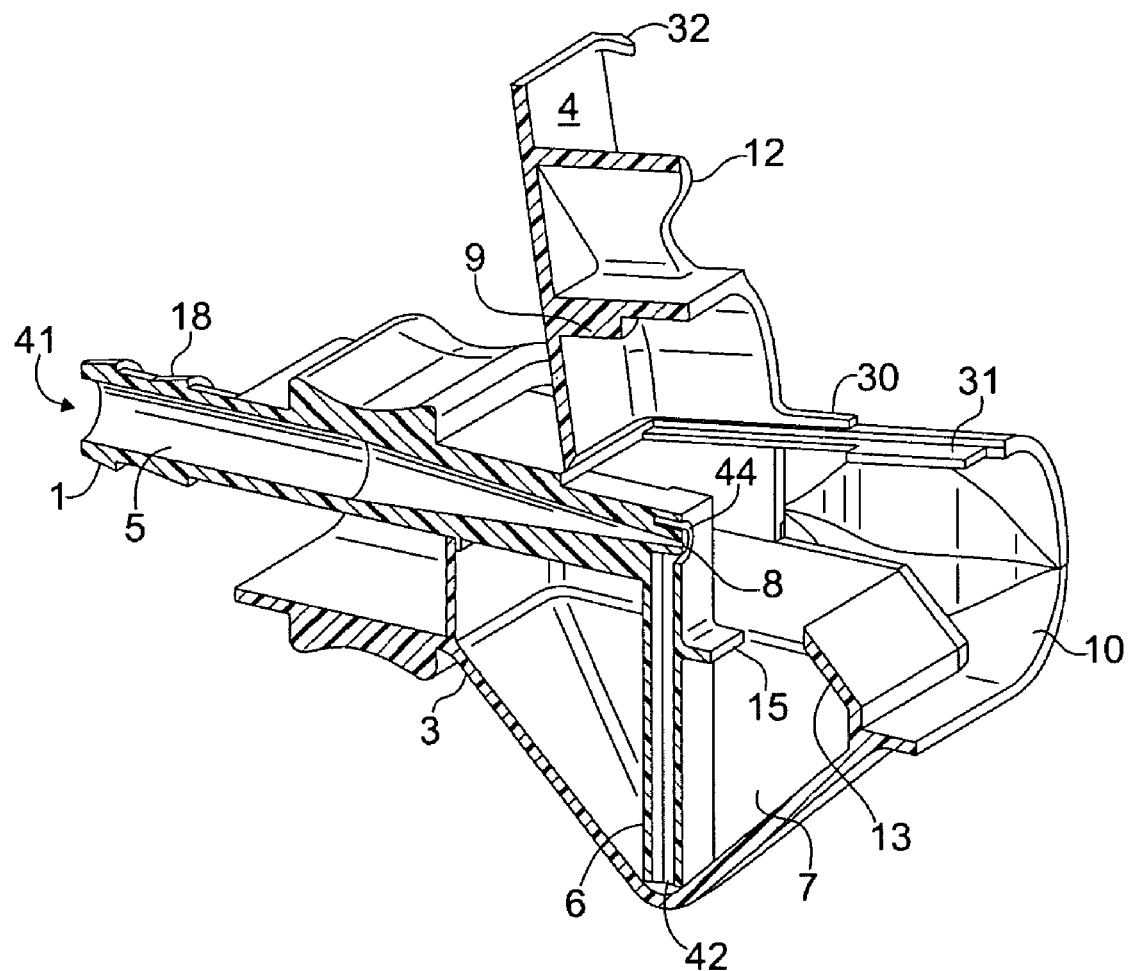
FIG. 7 schematically illustrates a cross-sectional view of the nebulizer of FIG. 6 taken along the sectioning line 7-7.

As seen in FIGS. 3 and 4, subsequent to particle creation, there are essentially two basic escape routes for a given particle. FIG. 3 shows the route F1 taken by a particle. This particle initially moves in a downward fashion. The baffle 15 helps to redirect particles and air flow away from the inlet end 42 of the siphon channel 6 so that the siphoning effect is not inadvertently shut down. If the particle is sufficiently small, it will follow the sinuous or tortuous path, F1, and will exit at the exit port 10 of the nebulizer 100. If on the other hand the particle is too large to follow the bulk flow out of the nebulizer 100, the particle will impact on an interior wall and will fall down into the reservoir 7 to be recycled. Note however that the path, F2, shown in FIG. 4 is representative of the primary exit path for particles generated within the nebulizer as determined by a reverse-flow geometry. For this case, a typical particle must essentially reverse direction after striking the impactor 9, moving back towards the direction of the inlet end 41 of the gas channel 5. However, since egress in that direction is prevented by a curtain wall 17, the only exit path is located at the exit port 10 of the nebulizer 100, and the particle must reverse direction again to move along the tortuous passageway indicated by F2 towards the direction of the exit port 10 to exit the nebulizer 100 via the exit port 10.

To guide the particle towards the exit port 10 along the direction shown by F2, a flow directing wall 12 may be provided in one or more of the upper and lower housing 2, 3, FIG. 4. The flow directing wall 12 may have an airfoil-type shape, with the tapered portion of the airfoil pointing in the downstream direction towards the exit port 10 of the nebulizer 100. Such an orientation of the flow direction will 12 may reduce the turbulence and backpressure of the air and mist as it moves out the exit port 10 of the nebulizer 100. Alternatively, the flow direction wall 112 may have the shape of a truncated airfoil having an open and 113 where the point of the airfoil would otherwise be located, FIG. 13. These direction reversals can create a very selective particle size filter that is believed to be largely responsible for the relatively small particles that are emitted from this nebulizer 100. Additionally, it has been observed that the particle size distribution is typically very narrow for the nebulizer 100 disclosed herein, which is a very desirable attribute.

The housing 40 of the nebulizer 100 may be fabricated from materials that possess surface tension properties characteristic of wetting materials to create a sheeting action that will facilitate the flow of recycled materials to the reservoir 7. For example, the material of the housing 40 may comprise plastics that are non-wetting in their original condition. Polyethylene (PE) and polypropylene (PP) are two examples. If the reservoir 7 is constructed of one of these materials, and has sufficiently steep internal shape, the liquid medication will roll down to the lowest point, which would presumably be the location from which the liquid medication is being siphoned. Many times however, in practical applications, after having been used, a surface that started out as non-wetting, can become fully or partially wetting due to the deposition of a very thin layer of dirt, minerals, or other contaminants on the surface. The surface might then act as a wettable one. For this reason, it is important to design the reservoir 7 to work well as a wettable material to start with.

The wetting angle of a wettable material is less than 90 degrees. The contact angle can be a very small angle as the edge of a liquid is pulled along a solid surface. Several characteristics of a wettable surface, together with intentional geometric features, can be used to help the functionality of the nebulizer design. An ideal nebulizer would have the capability to utilize every bit of the liquid medication contained therein. Achievement of this goal may be attempted by pulling the liquid medication from a location that is the lowest point in a depression of the reservoir 7. The inner walls of the reservoir 7 may be sloped as much as possible, because as the liquid medication level goes down, droplets of water can remain stuck in random locations on the walls of a reservoir 7 that is made from a wettable material. These droplets would be counted as wasted medication that the nebulizer 100 is unable to use as residual content. The nebulizer design can cause the air flow to move generally downward along the walls of the reservoir 7, which is generally a turbulent action. However the shear action downward along the reservoir wall will scrub the liquid down toward the pick up location.

Turning to FIGS. 14-22, additional configurations of a nebulizer in accordance with the present invention are illustrated, in which the impactor 109, 209, 309, 409 (collectively 109-409) includes a liquid feed channel 106, 206, 306, 406 (collectively 106-406) through which a liquid medication may be siphoned from the reservoir 107, 207, 307 (collectively 107-307) to be nebulized. As with the nebulizer 100 of FIGS. 1 and 2, the nebulizers of FIGS. 14-16 may include a nebulizer tube 101, an upper housing, and a lower housing 103-303, which may be configured to provide the reverse flow geometry described above with regard to FIGS. 3, 4. However, since the liquid feed channel 106-406 is included as a part of the impactor 109-409, the nebulizer tube 101 need not include a liquid feed channel, though it optionally may. In this regard, the nebulizer tube 101 includes a convergent gas channel 105 that may converge to a throat 108 in a manner similar to that illustrated with respect to the nebulizer tube 1 of the nebulizer 100 of FIG. 2. Also like the nebulizer 100 of FIG. 1, the throat 108 is oriented so that the output flow from the throat 108 strikes an impaction surface 119, 219, 319, 419 (collectively 119-419) of the impactor 109-409. The energetic collision generates the very fine, therapeutic particles required of nebulizers. It has been determined that a sufficiently small spacing is required between the throat 108 and impactor 109-409 to generate a fine mist. A suitable throat-to-impaction surface spacing is 10 to 30 mils.

Figure 14:
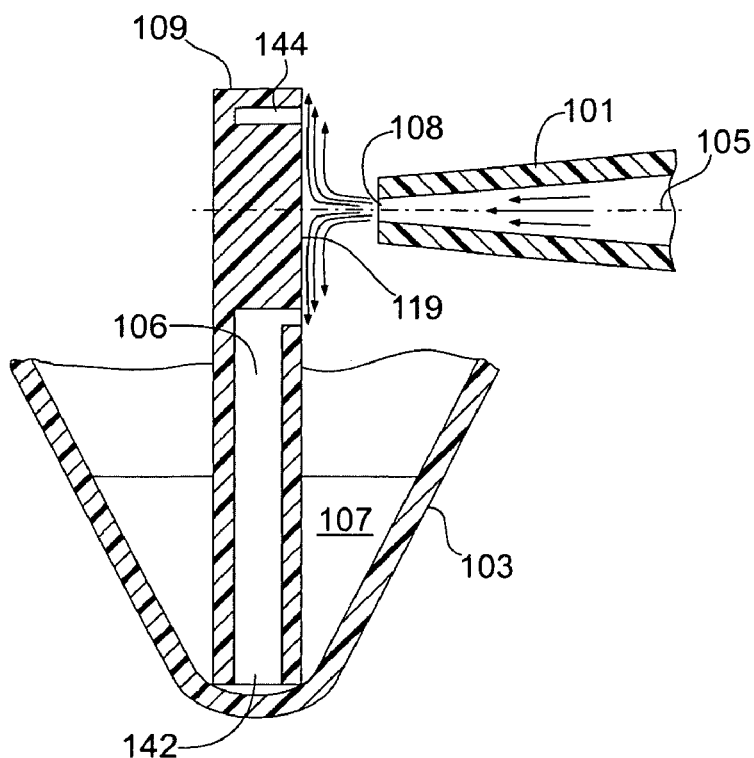
FIG. 14 schematically illustrates a fragmentary side cross-sectional view of an exemplary impactor in accordance with the present invention having in integrated siphon tube disposed proximate an exit nozzle.
Figure 15:
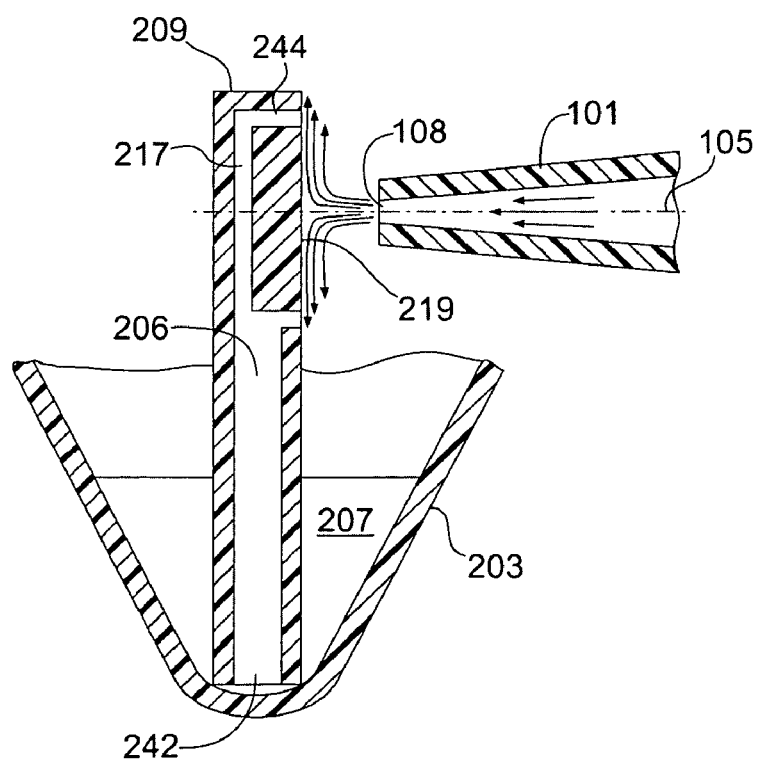
FIG. 15 schematically illustrates a fragmentary side cross-sectional view of another exemplary impactor in accordance with the present invention having in integrated siphon tube disposed proximate an exit nozzle.

The impactor 109-409 may be provided as a monolithic part of an upper or lower housing, such as lower housing 103, 203, 303 (collectively 103-303), FIGS. 14-16. The impactor 109-409 includes a liquid feed channel 106-406 having a first end 142, 242, 342, 442 disposed within the reservoir 107-307 of the lower housing 103-303 to receive medication to be nebulized. The opposing end of the feed channel 106-406 may be provided in the form of a slot exit, such as an annular slot exit 144, 244, 344, 444 (collectively 144-444), disposed proximate the throat 108 of the nebulizer tube 101. The slot 144-444 may be bound by an inner diameter of 75 mils and an outer diameter of 115 mils to yield a slot 144-444 having a radial width of 40 mils. An impaction surface 119, 219, 319, 419 (collectively 119-419) may be provided interior to the region defined by the annular slot exit 144-444. In certain configurations, it may be desirable to provide a liquid passageway 217, 317, 417 behind the impaction surface 219, 319, 419 that extends between the feed channel inlet end 242, 342, 442 and the exit slot 244, 344, 444 to provide a low resistance flow path for liquid to all locations along the annular exit slot 244, 344, 444. Such an arrangement may result in a flow that is more balanced; thus, energy in the gas flow may be more effectively transferred to the liquid to create a greater number of droplets.

In operation, the gas jet exiting the throat 108 impinges against the impaction surface 119-419 and spreads in a radially outward manner. The high-speed gas moves across the impaction surface 119-419 of the impactor 109-409 and across the opening of the annular slot exit 144-444. The Bernoulli principle causes liquid to be pulled into the air stream and an airborne mist is thus generated. The specific shape or topology of the impaction surface 119-419, inside or outside of the annular slot, can be varied in order to affect (statistical) droplet size, size distribution, speed, and direction. For example, the impaction surface 119, 219 may be flat, FIGS. 14, 15. Alternatively, the impaction surface 319 may be cusp-shaped, with the cusp aligned with the longitudinal axis of the nebulizer tube 101 to remove the dead zone on the impaction surface 319 intersection by the longitudinal axis of the nebulizer tube 101, i.e., a location directly across from the throat 108, FIG. 16. Still further, the impaction surface 419 may be cusp-shaped (with the cusp aligned with the longitudinal axis of the nebulizer tube 101) and concave so that the air jet leaves the impaction surface 419 at a slight angle to help create the low-pressure needed to pick up liquid from the annular exit slot 444, FIG. 17A. Alternatively, the impaction surface 519 of the impactor 509 may be concave and have no cusp, FIG. 17B. The dimensions and shape of the siphon exit can also be varied from the particular version shown.

Figure 18A:
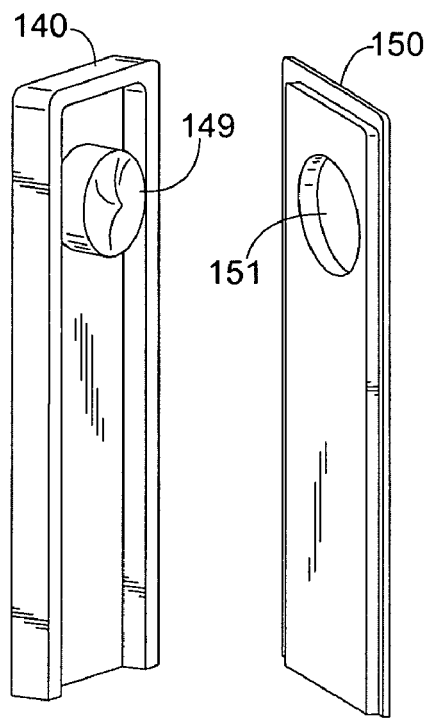
FIGS. 18A and 18B schematically illustrate an exploded view and an assembled view, respectively, of an exemplary impactor in accordance with the present invention having in integrated siphon tube.
Figure 18B:
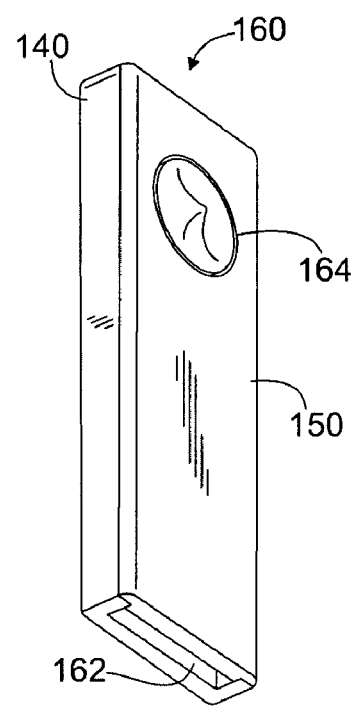
Figure 19:
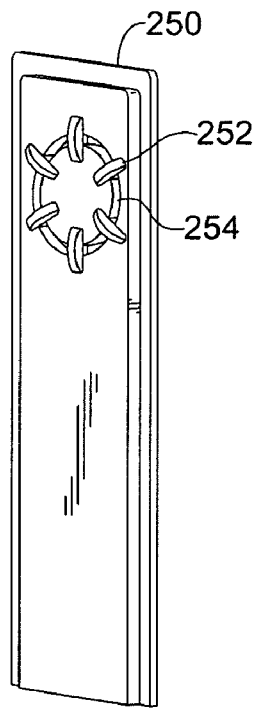
FIG. 19 schematically illustrates a perspective view of an exemplary impactor front plate in which the impactor is supported on the plate by a plurality of spokes.
Figure 20:
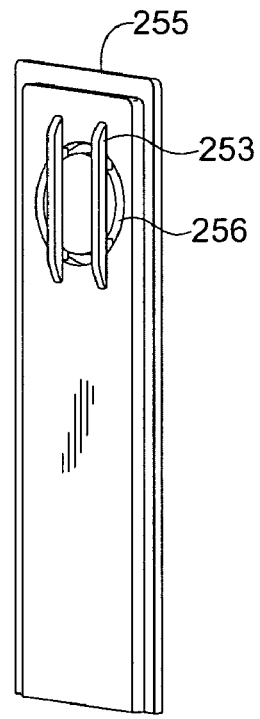
FIG. 20 schematically illustrates a perspective view of an exemplary impactor front plate in which the impactor is supported on the plate by a plurality of ribs.
Figure 21A:
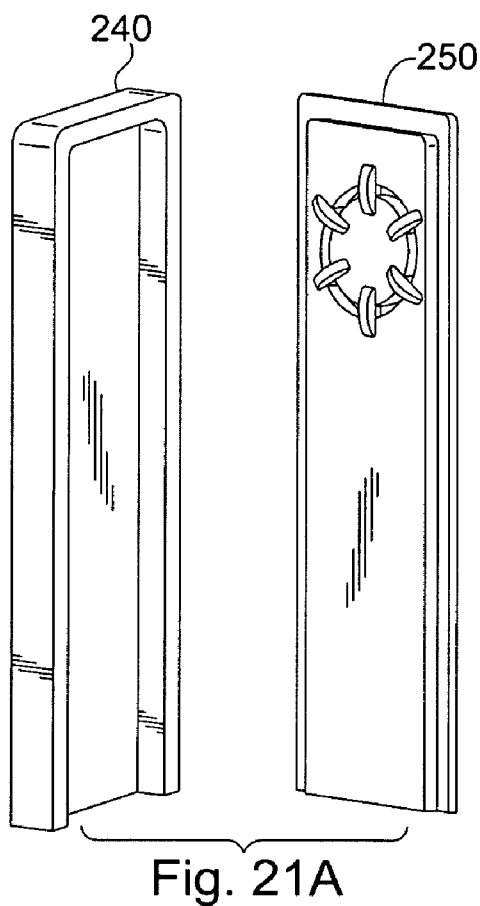
FIGS. 21A and 21B schematically illustrate an exploded view and an assembled view, respectively, of an exemplary impactor of the present invention using the front plate of FIG. 19 and having in integrated siphon tube.
Figure 21B:
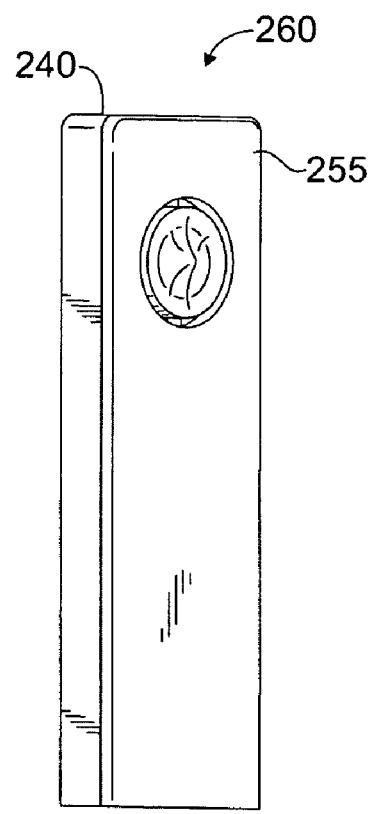
Figure 22:
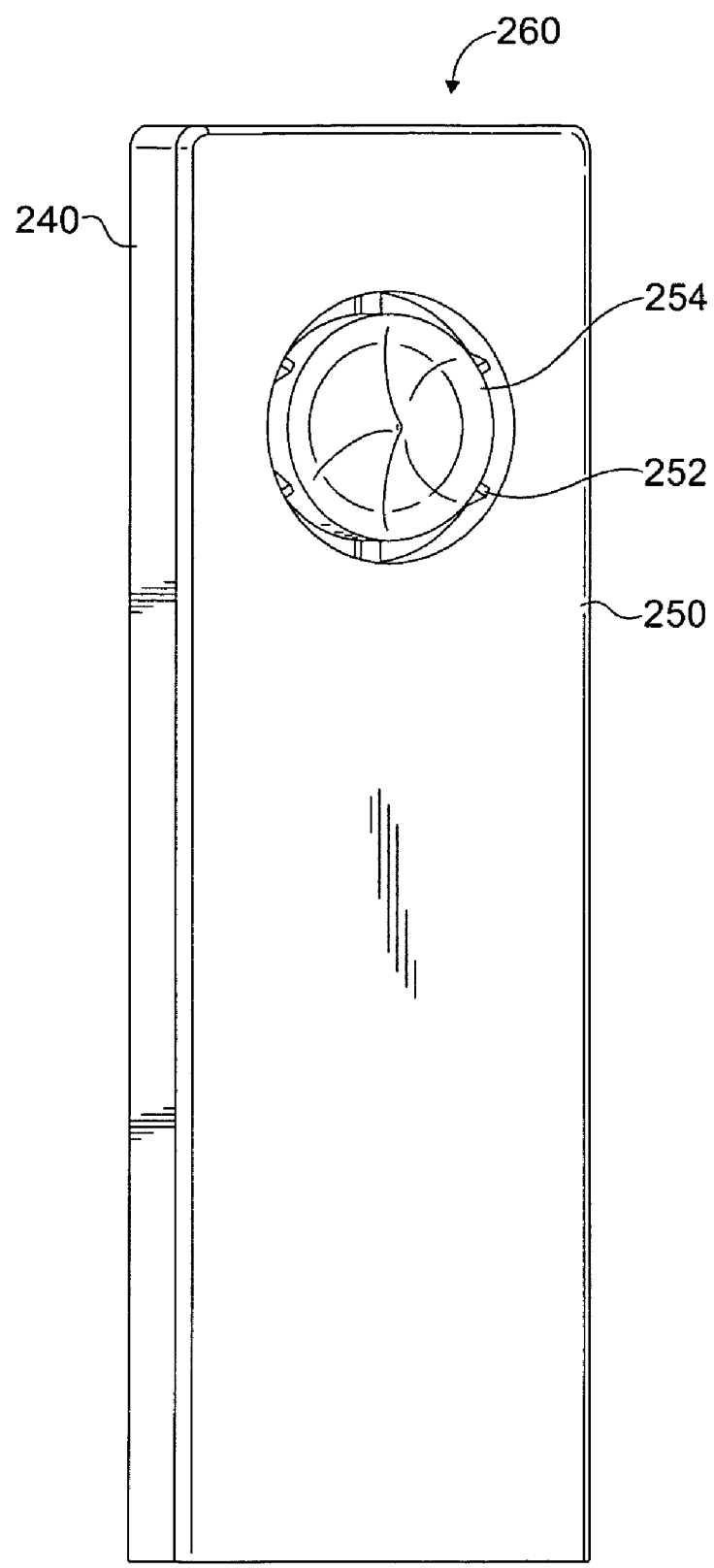
FIG. 22 further schematically illustrates the assembled view of the impactor of FIG. 20.

Turning now to FIGS. 18A and 18B, one configuration for providing an impactor of the type shown in FIG. 14 is illustrated. The impactor 160 may be provided in the form of a front cover panel 150 and a rear panel 140. The rear panel 140 may have a hollow, generally rectangular shape with a cylindrical raised portion to provide the impaction surface 149. A complementary mating cover panel 150 may have an opening 151 for receiving the impaction surface 149. The opening 151 may have a larger transverse dimension, e.g., diameter, than that of the impaction surface 149 to provide an annular gap 164 between the impaction surface 149 and opening 151. With the cover panel 150 in place over the rear panel 140, a liquid feed channel 162 is provided interior to the assembled impactor 160 which communicates with the annular gap 164. Alternatively, to provide impactor configurations which include a liquid passageway 217, 317, 417 behind the impaction surface 219, 319, 419, a front cover 250, 255 may be provided in which the impaction surface 254, 256 is supported on the front cover 250 via radial spokes 252 or ribs 253, FIGS. 19, 20. Thus, when assembled with a hollow, generally rectangular rear panel 240 liquid is able to flow behind the impaction surface 254, 256, FIGS. 21A, 21B, 22.

Some of the possible functional advantages of the configurations in which the impactor has a liquid feed channel include: less mixing of the gas and liquid streams prior to interaction with the impaction or other surfaces; the amount that the liquid/gas stream interacts with the impactor 109-409 can be more readily controlled; the direction of flow of the generated mist is favorable; and, the mist does not head directly toward the exit port of the nebulizer, with some filtering-out of larger droplets accomplished in a compact size. In addition, if the goal is improved functionality with less regard for complexity, a nebulizer might be designed with two siphon outlets. One siphon outlet would be near the end of the gas jet and a second as part of the impactor structure.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A nebulizer for delivering a mist of liquid, comprising:
   a housing;
   a reservoir disposed internally to the housing for containing a liquid to be nebulized by the nebulizer;
   a nebulizer tube having:
      a gas channel, the channel including a first end for receiving compressed gas and a second end for expelling compressed gas, the gas channel extending along a longitudinal axis from a first end to a second end of the nebulizer tube, and
      a liquid feed channel having a first end in fluid communication with the reservoir for receiving the liquid from the reservoir and having a second end disposed proximate the second gas channel end; and
   an impactor disposed proximate the second end of the nebulizer tube, the impactor having an impaction surface disposed at an inclined, non-orthogonal angle relative to the longitudinal axis of the nebulizer tube,
   whereby expulsion of compressed gas from the second end of the gas channel onto the impactor creates a siphon in the liquid feed channel to draw liquid into the feed channel and to expel the liquid and compressed gas from the second end of the nebulizer tube to nebulize the expelled liquid when the expelled liquid strikes the impactor, and wherein the second end of the liquid feed channel comprises an annular passageway disposed about the second gas channel end, whereby the expulsion of gas from the second end of the gas channel onto the impactor creates a siphon in the liquid feed channel to draw liquid into the feed channel and to expel the liquid from the second end of the feed channel.

2. A nebulizer for delivering a mist of liquid, comprising:
   a housing;
   a reservoir disposed internally to the housing for containing a liquid to be nebulized by the nebulizer;
   a gas channel disposed within the housing, the channel including a first end for receiving compressed gas and a second end for expelling compressed gas; and
   an impactor disposed proximate the second end of the gas channel, the impactor including a liquid feed channel having a first end in fluid communication with the reservoir for receiving the liquid from the reservoir and having a second end disposed proximate the second gas channel end,
   whereby expulsion of compressed gas from the second end of the gas channel onto the impactor creates a siphon in the liquid feed channel to draw liquid into the feed channel and to expel the liquid from the second end of the liquid feed channel to nebulize the expelled liquid, and wherein the impactor comprises an air baffle disposed between the first and second ends of the liquid feed channel to deter liquid being blown away from the first end of the liquid feed channel by the air flow from the second end of the gas channel.

* * * * *